United States Patent [19]

Pizatella et al.

[11] 3,998,100
[45] Dec. 21, 1976

[54] EXERCISE PROCESS AND APPARATUS

[76] Inventors: Robert F. Pizatella, 909 Coleman Ave.; E. A. Johnson, 99 Sterling Road, both of Fairmont, W. Va. 26554

[22] Filed: Apr. 21, 1975

[21] Appl. No.: 569,691

[52] U.S. Cl. .................................................. 73/379
[51] Int. Cl.² .......................................... G01L 5/02
[58] Field of Search .............. 73/379; 272/72, 79 C

[56] References Cited

UNITED STATES PATENTS

| | | | |
|---|---|---|---|
| 3,465,592 | 9/1969 | Perrine | 73/379 |
| 3,495,824 | 2/1970 | Cuinier | 73/379 X |
| 3,848,467 | 11/1974 | Flavell | 73/379 |

*Primary Examiner*—James J. Gill
*Attorney, Agent, or Firm*—Carothers and Carothers

[57] ABSTRACT

A process and apparatus for isokinetic muscular exercise wherein the speed of the exercise movement and the resistive forces are regulated to preset or predetermined values which are adjustable throughout the exercise movement in accordance with an exercise program tailored to the skill and requirements of the exerciser. When the exerciser does not meet the prescribed minimums in the program performance, the exercising apparatus automatically provides assistance so that he will maintain the programmed rate of movement. The exerciser is classically conditioned to maximum ability by administration to him of a disciplinary conditioning signal that is proportional to the amount of assistance required to be administered by the machine.

13 Claims, 2 Drawing Figures

EXERCISE PROCESS AND APPARATUS

BACKGROUND OF THE INVENTION

This invention is related generally to a process for active resisted exercise and to an exemplary apparatus for performing such a process.

A number of processes of exercise and exercise apparatus have been developed over the years wherein an external force is applied to the body to oppose forced muscular contractions thereby developing an increase in muscle power and hypertrophy.

In conducting such exercises, the external applied force is either dynamic or static. The method and apparatus of the present invention relates to dynamic exercising wherein the person exercising resists a yielding force. In such dynamic exercising equipment, it has been recognized that the muscle is not equally powerful throughout its entire range of motion and that the resistive force should vary as the output force of the person exercising. In this regard, attention is directed to U.S. Pat. No. 3,465,592 issued to James J. Perrine on Sept. 9, 1969.

The object of the Perrine invention is to provide a process and apparatus for exercising which will oppose the movement of the person exercising throughout the full range of movement of the muscle, and which will afford any desired, adjustable, resistive force which the person exercising is capable of overcoming and which will also be in equilibrium with the person's applied force, avoiding recoil or unbalancing effects.

Perrine accomplishes this objective by permitting the speed of an exercise movement to accelerate essentially unopposed by resistive forces from zero to a preset or predetermined rate of speed, and any magnitude of muscular force tending to accelerate the exercise movement beyond the predetermined rate of speed is counteracted by the exercise system. Thus, the Perrine process establishes a maximum rate of speed obtainable regardless of the magnitude of muscular force applied by the subject by counteracting any magnitude of applied muscular force tending to accelerate the movable exercising member beyond a predetermined rate of speed.

SUMMARY OF THE INVENTION

While it is an object of the present invention to accomplish the same broad objectives set forth in Perrine, the present invention accomplishes those objects in a different manner and in addition accomplishes other objects not heretofore contemplated by the prior art.

The present invention provides an apparatus and process for the classical conditioning of a subject working in isokinetic exercise which is conducted by moving an object of opposing force along a path when a muscular force is applied thereto. The object to be moved or exercised upon is engaged by a portion of the subject and moved along a path and is opposed by a predetermined resistance force. When the subject is unable to move the object at the predetermined rate of speed, the opposed resistance force is automatically decreased and positive assistance is given in a sufficient amount to force the subject to move the object at the pre-programmed predetermined rate. However, a disciplinary conditioning signal is administered to the subject in magnitude that is proportional to the magnitude of the rate of speed at which the object being moved falls below the predetermined rate or proportional to the amount of assistance that is being supplied by the apparatus to maintain the prescribed speed.

In this manner, the subject is not only experiencing physical conditioning, but in addition he is also having a mental experience which is considered quite necessary in order to condition the subject to establish a mental path or habit to be followed or experienced as opposed to a mere physical experience. Thus, by regulating the speed and administering disciplinary measures to the subject or person exercising when he falls below the predetermined rate of speed set for him, the present invention thus establishes a desired habit of exercise from said experience. It is the belief of the inventors that the brain of the exerciser must be conditioned to experience what his body can do before he can actually attain the desired physical condition whereby the exerciser can move the object of opposing force at the predetermined rate of speed which was originally set as the subject's goal. The method and apparatus of the present invention permits the subject to mentally experience the reality of attaining his goal and encourages him through classical conditioning to attain that goal.

The apparatus of the present invention operates on the premise that an exerciser will accept a pattern for speed, strength, and coordination if all of his sensations are constantly confronted with it. In other words, that the entire body including the motor brain cells and the voluntary and involuntary muscles must experience some sensation of speed, strength and coordination before fully developing in those areas. The apparatus of the present invention is capable of sensing the exact moment that the subject fatigues, i.e., is no longer able to manipulate a preset weight in the prescribed or preprogrammed manner. At the precise moment that the individual fails to handle the weight properly, the apparatus automatically assists the exerciser to permit him to perform extra strenuous repetition of the exercise. The apparatus will alleviate only that portion of the load over the maximum weight which he can properly move in the preprogrammed manner or at the preset rate of movement goal which the exerciser experiences at that precise moment of fatigue yet forces him to continue his movement at the prescribed rate of speed. Thus, the exerciser is permitted a handicap of only the overload. However, in accepting that handicap, the exerciser may also be subjected to a disciplinary classical conditioning signal which is proportional in magnitude to the handicap he has received thereby subjecting him with an adverse stimulus to encourage him to attain his individually tailored goal.

The apparatus of the present invention generally comprises a first means for operative engagement and movement by a portion of the person exercising for back and forth movement in opposite directions of positive and negative lift, respectively, and between extreme positions within reach of the portion of the person exercising, and second means operative when the first means is being moved by the person exercising in at least one direction for simultaneously establishing a predetermined minimum of magnitude of muscular exertion required by the person exercising and a predetermined maximum rate of speed obtainable by the first means in the direction of exercise. It is further desirable that the magnitude of exertion and rate of speed for one direction of exercise be independently controllable from those predetermined values set for the other direction of exercise in order to provide the greatest amount of versatility in the apparatus.

BRIEF DESCRIPTION OF THE DRAWINGS

Other objects and advantages appear in the following description and claims.

The accompanying drawings show, for the purpose of exemplification without limiting the invention or the claims thereto, certain practical embodiments illustrating the principles of this invention wherein:

DETAILED DESCRIPTION OF THE DRAWINGS

Figure 1:
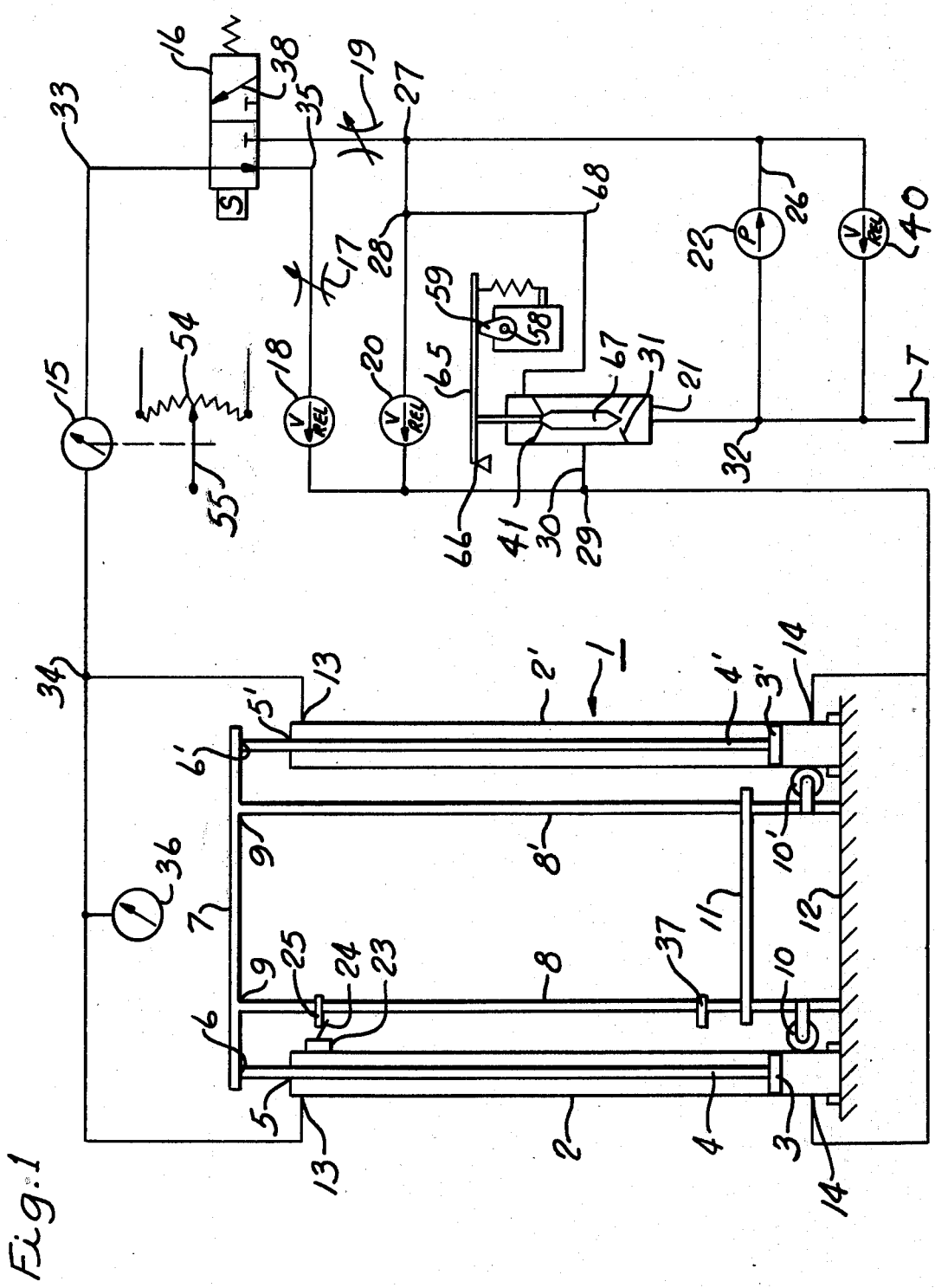
FIG. 1 is a combined diagrammatic and schematic view illustrating the hydraulic operation of one embodiment of the classical conditioning exercising apparatus of the present invention.

Referring to FIG. 1, the exercising apparatus of the present invention consists primarily of the mechanical exercising apparatus 1 in combination with the remaining hydraulic circuitry which controls the operation of the apparatus 1.

Exercise apparatus 1 is comprised of two parallel vertically-disposed hydraulic cylinders 2 and 2' which contain respectively pistons 3 and 3'. Each of the pistons is provided with a respective elongated piston rod 4 and 4' which extend upwardly in a sealed manner through the top of cylinders 2 and 2' respectively as indicated at 5 and 5'. The top ends 6 and 6' of the piston rods 4 and 4' are in turn rigidly secured to the top cross bar member 7 which will accordingly rise and fall with the movement of pistons 3 and 3' and which also maintains pistons 3 and 3' in an aligned relationship such that they will always move simultaneously.

Spaced vertical bars 8 and 8' are rigidly secured at their top ends 9 and 9' to the top cross bar 7 and the bottom of the vertical bars 8 and 8' are secured to rollers 10 and 10', which are permitted to free wheel against the insides of cylinders 2 and 2' respectively, in order to guide the lower ends of vertical bars 8 and 8' in a friction free manner when the entire assembly consisting of pistons 3 and 3', piston rods 4 and 4', top cross bar 7 and vertical bars 8 and 8' are simultaneously raised or lowered. This entire assemblage is raised and lowered by the exerciser by means of the adjustable hand bar 11, which is grasped by the exerciser to raise and lower the aforesaid assemblage in much the same manner that a weight lifter would raise and lower a conventional barbell.

Hand bar 11 is adjustable in relation to its vertical position on vertical bars 8 and 8'. Hand bar 11 may be slid up or down vertical bars 8 and 8' and adjusted to any predetermined level or height desired and there temporarily locked in firm engagement with vertical bars 8 and 8' by any conventional locking means.

The bottom of the mechanical exercise apparatus 1 is illustrated as being supported rigidly on the ground surface 12. However, it is obvious that this mounting arrangement may be modified by pivotally supporting the bottom of cylinders 2 and 2' from the ground surface 12 in order to permit the entire apparatus 1 to be tilted forward or backward as may be desired by the person conducting exercises on the apparatus in order to accomodate a particular exercise which could not ordinarily be accomplished should the entire apparatus 1 be rigidly mounted to the floor or ground surface 12.

The hydraulic circuitry of the apparatus consists primarily of the aforesaid elongated hydraulic cylinders 2 and 2' which are provided with hydraulic fluid access and egress above and below the pistons 3 and 3' as indicated at positions 13 located above the pistons 3 and 3' and positions or connections 14 located below the pistons 3 and 3'. Continuing along the hydraulic circuit, the primary hydraulic components further comprise fluid flow sensor 15, the solenoid operated valve 16, upstroke adjustable flow control 17, upstroke pressure control valve 18, downstroke adjustable flow control 19, downstroke pressure control valve 20, modulating valve 21, hydraulic pump 22 and tank or reservoir T. Pressure relief valve 40 is merely a safety pressure relief valve which will activate to dump fluid to tank T should a maximum safety pressure be obtained due to a failure in the system.

The apparatus as pictured in FIG. 1 is shown at its rest position with the bottom of vertical bars 8 and 8' resting on the floor 12 as a stop means. Of course, any other type of typical stop arrangement may be provided such as having the underside of top cross bar 7 strike the top surface of the cylinders 2 and 2'. The apparatus is illustrated in a stage of readiness just prior to the time that the exerciser will engage the cross bar or hand bar 11 and begin to apply the necessary muscular force required to raise the same at the predetermined rate. At this position or stage, electrical switch 23 which is provided with contact toggle 24 extending therefrom, is positioned at the top inside of hydraulic cylinder 2 and toggle 24 is held in a full down position by reason of engagement with upper adjustable limit 25 which may be slid vertically up and down on bar 8 and then locked into clamped engagement therewith once the desired limit set has been obtained.

Switch 23 is basically a two-position switch, one position for up and one for down. However, the switch is so constructed such that toggle 24 may be held downward against a spring bias as indicated in FIG. 1 to provide a third switching function of completely disengaging the fluid flow sensor 15, which in turn controls the modulating valve 21, while the machine is not in actual use or the hand bar 11 is not being raised by a subject. This switch position is indicated as 53 in the electrical circuit diagram of FIG. 2 and will be explained further on in relation to that figure.

At the point in time depicted in FIG. 1, hydraulic pump 22 is continually operating, but it is bypassing its fluid flow through down pressure control valve 20, which is actually merely one form of a pressure release valve, to tank T, via modulating valve 21. In other words, the hydraulic fluid is pumped from 22 via lines 26, 27 and 28 to down pressure control valve 20 which permits the passage of the fluid under pressure therethrough when the preadjusted requisite pressure set by the valve 20 has been attained and the fluid passes thereon through lines 29 and 30 through modulating valve 21, which is shown in its normally closed position, via the open valve seat 31 at the bottom of modulating valve 21 through line 32 to tank T or back into the hydraulic pump 22. Line 27 is cut off at the top by means of solenoid operated valve 16 as indicated so that the fluid under pressure emitting from pump 22 does not reach the upper surface of pistons 3 and 3' via line 33.

Figure 2:
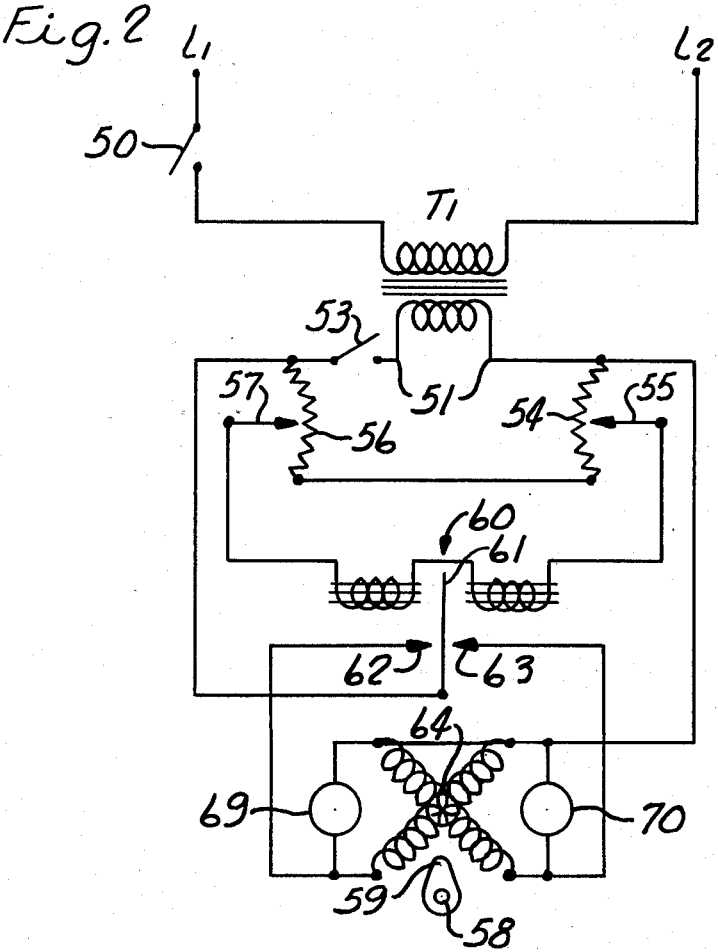
FIG. 2 is an electrical schematic diagram of a portion of the electrical circuitry which is utilized in the operation of the embodiment illustrated in FIG. 1.

As soon as the person conducting the exercise begins to raise hand bar 11, spring biased toggle 24 is permitted to return upwardly to its normal down position thereby closing switch 53 of FIG. 2 thereby activating the fluid flow sensor 15 which in turn controls modulating valve 21. Fluid flow sensor 15 and modulating valve 21 make up the heart of the machine's capability of assisting the subject by relieving him of the overload when he fatigues.

Fluid flow sensor 15 having been energized on bar 11 being initially raised by the subject, and the entire hydraulic system being full of the necessary fluid, pistons 3 and 3' force the fluid from cylinders 2 and 2' under pressure through connections 13 into line 34. The flow rate of the fluid through lines 34 and 33 is accordingly sensed or detected by fluid flow sensor 15. The fluid flow continues on through solenoid operated valve 16 which is biased to its normally off position due to the fact that switch 23 remains in its normally down or off position. The primary function of switch 23 is to operate solenoid S of valve 16.

The fluid flow continues on through valve 16 into line 35 where it then passes through the upstroke flow control 17 on to the upstroke pressure control valve 18.

Flow control 17 is preadjusted to a program tailored to the particular person conducting the exercises in order to set the maximum flow permitted through the control 17, or in turn, the maximum rate of rise permitted for hand bar 11 by the subject. Flow control 17 (as well as flow control 19) is an adjustable pressure compensated restriction valve which maintains the maximum flow permitted through the control constant regardless of the pressure applied thereto. This flow control 17, of course, does not have to be preset to one value, and may be varied through the full upward stroke of hand bar 11 as desired, such as by computer control to tailor fit an exercise program for the particular subject.

Up pressure control valve 18 is also adjustable and is either preset to one value or preset to a series of program values by computer or the like, to regulate the up pressure which must be applied to hand bar 11 before the same will even begin to move upwardly. Thus, as the subject begins to apply muscular force upwardly on hand bar 11, he must push with sufficient muscular strength to overcome the preset value of up pressure control valve 18 before the bar will begin to move. Once the bar begins to move upwardly due to valve 18 permitting flow therethrough, then flow control 17 regulates the maximum possible rate of speed with which hand bar 11 may be raised at any particular moment. In conducting the exercise, the subject may directly read the amount of muscular force he is applying to hand bar 11 by reading the pressure gauge 36 over top of the apparatus 1. This pressure gauge is correlated to read the pressure within the hydraulic system in terms of pounds.

As the subject is lifting hand bar 11, the fluid flowing from the top portion of cylinders 2 and 2' passes through flow control 17 and relief valve 18 and is thereupon permitted to flow either in the bottom portion of cylinders 2 and 2' below pistons 3 and 3' via line 29 to provide positive assistance so that the exerciser is forced to maintain the prescribed rate of speed, or to flow on through line 30 to tank via modulating valve 21 (past open valve seat 31) and line 32.

Up pressure control valve or pressure relief valve 18 thus regulates the amount of weight which the person exercising must lift by applying muscular force to cross bar or hand bar 11, and flow control 17 regulates the maximum rate of speed at which he can possibly raise weighted bar 11.

Once the subject has reached the top extremity of his exercise stroke with bar 11, limit 37 engages toggle 24 of switch 23 and immediately switches on solenoid S of valve 16 thereby sliding valve 16 over to the left position from the right-hand position as viewed in the figure.

At this point in time, the fluid being pumped from pump 22 is now permitted to flow through down flow control 19 via line 27 on through passage 38 of valve 16 into line 33 and 34 on into the upper half of cylinders 2 and 2' via connections 13, thereby applying the pressure or weight regulated by down pressure control valve or relief valve 20 to the top of pistons 3 and 3'. Thus, down flow control 19 regulates the maximum speed at which the bar or hand bar 11 may be lowered by the subject in the same manner that flow control 17 regulates the maximum rate at which the hand bar 11 may be raised and valve 20 determines the amount of weight which the subject must resist on the down or negative stroke in the very same manner which valve 18 regulated the amount of weight the subject must lift on the upper positive stroke. The only reason separate pressure and flow controls are provided for the up and down strokes respectively is in order to provide more versatility to the apparatus so that the subject may select different pressure and flow rates for the up and down strokes. It is generally known that a subject can handle more weight on the down or negative stroke than he can handle on the up or positive stroke, and therefore, for example, relief valve 20 may be adjusted so that it requires a higher pressure within the system than would relief valve 18, and flow control 19 might, for example, be adjusted so that it would permit a slower rate of descent of hand bar 11 than flow control 17 would permit on the up or positive stroke.

Fluid flow sensor 15 is adjusted to only detect overloads being applied to the subject by detecting how much less the flow rate is in lines 34 and 33 that the prescribed maximum rates set at that time for flow controls 17 or 19, whichever the case may be. Thus, for example, if during an up or positive stroke of bar 11 by the subject, the flow rate at that moment through flow-sensor 15 is less than the rate prescribed by flow control 17, then this differential is detected, and a corresponding electrical signal of proportional value is generated and utilized to provide two things; first of all, to open modulating valve 21 from its normally closed position as shown in FIG. 1 to permit or provide the subject with some assistance to the degree of overload he is experiencing, and secondly to generate a disciplinary signal, such as an audible signal, which is also in proportion to the degree of overload that the machine is handicapping him with, and this signal is applied to the subject for disciplinary conditioning measures.

Referring in addition to FIG. 2, this figure shows a simplified schematic diagram of the electrical operation performed by the fluid flow sensor 15. A common supply of AC house current is applied to lines L1 and L2. A simple on-off switch 50 is provided to turn the apparatus on and off and may also be utilized to control the power supply to solenoid S and to pump 22 if desired.

The line voltage is fed to step down transformer T1 where it is reduced at its output 51 to a more desirable low voltage for use in the fluid flow sensing system. Switch 53 will be in its closed position during operation of this system as previously explained, when bar 11 is being raised due to the fact that upper limit 25 is not in engagement with switch 23.

Fluid flow sensor 15 detects the difference between the flow rate actually occurring in lines 34 and 33 and that which is preset by control 17 and indicates this amount of variance accordingly on potentiometer 54 by varying contact arm 55 of the potentiometer accordingly. This potentiometer is illustrated also in FIG. 1. Fluid flow sensor 15 may, for example, detect flow by pressure differentials on opposite sides of a restriction. Honeywell Model P906A Differential Pressuretrol (trade mark) controller may be used for flow sensor 15. This particular model also includes potentiometer 54 and contact arm 55.

With further reference to FIG. 2, a second potentiometer 56 is illustrated at the left of the figure and is also provided with a similar rotatable contact arm 57. Contact arm 57 is rigidly ganged with the shaft 58 of cam 59, which is illustrated in both figures. This potentiometer together with the motor driving cam 59, modulating valve 21, potentiometer 56, contact arm 57, and elements 65 and 66 may be provided by a combination, for example, of Honeywell specialized three-way valve with control linkage Model No. 1606 together with Model No. M944 Modutrol (trade mark) motor.

Potentiometers 54 and 56 are always placed in a balanced condition. In other words, if arm 55 of potentiometer 54 moves in one direction by reason of a detection of a rate difference through fluid flow sensor 15, then correspondingly contact arm 57 of potentiometer 56 must also move. This is accomplished by means of the balanced relay 60. When the circuit is unbalanced one way or another by means of a deflection in contact arm 55 of potentiometer 54, then relay contact 61 will accordingly be deflected one direction or the other in correspondence with the direction of deflection made by contact arm 55, thereby closing the circuit with either contact 62 or 63 causing cam 59 to correspondingly rotate either left or right by corresponding energization of the shaded pole motor 64 having aforementioned shaft 58.

Referring back to FIG. 1, when cam 59 rotates in either direction, spring biased lever 65 which is fulcrumed at 66 is permitted to lower thereby closing the modulating valve plunger 67 against the bottom seat 31 of the valve and opening the upper seat 32 thereby permitting the passage of fluid under pressure from pump 22 via lines 26, 27 and 68 to the upper portion of modulating valve 21 past upper seat 41 and valve plug 67 on into line 30 and from there through line 29 to the underside of pistons 3 and 3' of apparatus 1. Thus, a corresponding amount of pressure is applied to the underside of pistons 3 and 3' to assist the subject and thereby force him to maintain the prescribed rate of speed and pattern of movement.

However, once the subject has been assisted, he will be immediately able to raise hand bar 11 at the proper predetermined or preset rate of speed and at that point fluid sensor 15 will immediately sense this and return potentiometer contact arm 55 back to its normal position and thereby also unbalance relay 60 causing motor 64 to energize and rotate cam 59 back the other direction to its normal position as indicated in FIG. 1. Thus, modulating valve 21 is returned to its normally closed position with plug 67 tight against upper seat 41 and thus the subject is once again left without any handicap until such time that he fatigues to a sufficient point to permit the process to repeat itself.

A similar process also occurs on the down stroke once lower limit 37 energizes switch 23 to in turn energize solenoid S and operate the valve 16. However, in this situation where the hand bar 11 is being lowered, the fluid flow sensor 15 operates to provide assistance to the subject to prevent the bar 11 from falling at its full rate determined by fluid flow control 19 as here the object is not to permit the machine to do the work for the subject, and if the subject permits the bar to fall too rapidly, then flow sensor 15 will detect that the flow rate differential actually occuring between that in lines 33 and 34 and that set by down flow control 19 is not sufficiently large, and arm 55 will deflect and modulating valve 21 will be opened and permit the application of the overload pressure to the bottom of pistons 3 and 3' thereby helping the subject to slow his rate of descent. Thus in the down or negative stroke, sensor 15 detects an increase in rate of flow over a predetermined sensor flow rate which correlated in turn to be less than that set for flow control 19 by a predetermined amount. However, on the up stroke, sensor is operative to detect a decrease in rate of flow with direct reference to the flow rate set by flow control 17.

With further reference to FIG. 2, classical conditioning signals 69 and 70 are provided to create an irritable signal, either audible or visual or both, or any similar signal such as electric shock, which is applied to the subject as a disciplinary conditioning signal. Thus, when relay 60 is unbalanced, or cam 59 is not in its normal stable position, an irritating conditioning signal will be applied to the subject which is preferably in a magnitude proportional to the amount of assistance or handicap which the subject is receiving. The signal is preferably produced such that the greater the displacement of cam 59 the more irritating the signal becomes. However, the circuit of FIG. 2 is specifically shown such that signals 69 and 70 will give a signal of continous magnitude. To proportionately vary the magnitude, those skilled in the art will appreciate that the voltage applied to signals 69 and 70 may be proportionately varied through a potentiometer regulated by the movement of cam 59 or shaft 58.

We claim:

1. Apparatus for use in muscular exercise including a supporting surface and an exercise apparatus mounted on said supporting surface, said exercise apparatus comprising: first means for operative engagement and movement by a portion of the person exercising for back and forth movement in opposite directions of positive and negative lift respectively between extreme portions within reach of said portion of said person exercising along a predetermined path of movement; second means operative when said first means is being moved by said person exercising in at least one of said opposite directions, for simultaneously establishing a predetermined minimum of magnitude of muscular exertion required by the person exercising on said first means and a predetermined maximum rate of speed obtainable by said first means in a direction of exercise, assistance means becoming operative upon said first means being moved in the direction of positive lift exercise by said person exercising at a rate of speed less than said predetermined rate to apply positive movement to said first means in the direction of exercise to meet said predetermined rate; and classical conditioning means responsive to said decrease for administering a disciplinary conditioning signal to said person exercising.

2. The apparatus of claim 1 wherein said second means is operative in both of said directions of exercise.

3. The apparatus of claim 2 wherein said predetermined magnitude of exertion and rate of speed for one direction of exercise are independently controllable in said second means from those predetermined values for the other direction of exercise.

4. The apparatus of claim 1 wherein said assistance means also becomes operative upon said first means being permitted to move in the opposite direction of negative lift exercise by said person exercising at a rate of speed more than a preset limit which is less than said predetermined rate of speed to increase the resistance to movement of said first means in the direction of exercise to maintain said preset limit; said classical conditioning means responsive to said increase for administering a disciplinary conditioning signal to said person exercising.

5. The apparatus according to claim 1 further including means for measuring said muscular exertion by said exerciser on said first means.

6. The apparatus according to claim 1 wherein said first means is a horizontal bar.

7. The apparatus according to claim 1 wherein said first means includes two portions adapted to be gripped by the hands of said exerciser and a mechanism mounting said portions of said first means substantially equidistant from said supporting surface.

8. An apparatus for isokinetic muscle exercise of a subject by use of means movable along a path when a muscular force is applied thereto, said apparatus comprising:
means movable along a predetermined path, movement of said movable means along said path being initiated and maintained by a subject exercising applying a muscular force thereto;
means for detecting the decrease in rate of speed of said movable means below a predetermined rate of speed;
means applying a positive force to said movable means for acceleration thereof to said predetermined rate along said path in proportion to the detected decrease in rate of speed of said movable means below said predetermined rate; and
classical conditioning means responsive to said decrease in rate of speed for administering a disciplinary conditioning signal to said person exercising.

9. An apparatus for use in muscular exercise comprising:
a support;
grip means for engagement and movement under applied muscular force by a person exercising;
first means coupling said grip means to said support for movement along a predetermined path by said person exercising;
second means operative when said grip means is being moved along said path by a muscular force applied by said person exercising for precluding movement of said grip means along said path beyond a speed greater than a predetermined rate;
third means for sensing a decrease of magnitude of said muscular force applied by said person exercising and imparting positive movement to said grip means along said path to said predetermined rate when said decrease in muscular force is less than a predetermined magnitude; and
classical conditioning means responsive to said decrease in muscular force for administering a disciplinary conditioning signal to said person exercising.

10. Apparatus for use in musclar exercise comprising;
a support;
grip means for engagement and movement under applied muscular force by a person exercising;
first means coupling said grip means to said support for movement along a predetermined path by said person exercising;
assistance means imparting positive acceleration to said grip means to a predetermined rate of speed when the magnitude of muscular force applied to said grip means by said person exercising is less than that required to attain said predetermined rate of speed; and
classical conditioning means responsive to said lack in muscular force for administering a disciplinary conditioning signal to said person exercising.

11. Apparatus for use in muscular exercise comprising:
a support;
grip means for engagement and movement under applied muscular force by a person exercising;
first means coupling said grip means to said support for movement in opposite directions along a given predetermined path;
assistance means imparting positive acceleration to said grip means to meet a predetermined rate of speed in at least one of said opposite directions so as to establish said predetermined rate of speed when the magnitude of muscular force applied to said grip means by said person exercising is insufficient; and
classical conditioning means responsive to said insufficient magnitude of applied muscular force to administer a disciplinary conditioning signal to said person exercising.

12. Apparatus for use in muscular exercise comprising:
a support;
grip means for engagement and movement under applied muscular force by a person exercising;
first means coupling said grip means to said support for movement along a predetermined path by said person exercising;
second means operative when said grip means is being moved along said path by a muscular force applied by said person exercising for precluding movement of said grip means along said path beyond a speed greater than a predetermined rate;
third means for sensing the magnitude of said muscular force being applied to said grip means and for positively moving said grip means along said path at said predetermined rate of speed when said applied muscular force is less than a predetermined magnitude; and
classical conditioning means responsive to the magnitude of said applied muscular force below said predetermined magnitude for administering a disciplinary conditioning signal to said person exercising.

13. A process of classical conditioning isokinetic exercise of a subject by the use of means movable along a path when a muscular force is applied thereto, said process comprising the steps of:
engaging with a portion of the subject a movable means which is put in motion by a muscular force applied thereto by said subject;

moving said movable means by the engaged portion of said subject along a predetermined path, said movable means being moved along said path opposed by a predetermined resistance force;

increasing the rate of movement of said movable means to a predetermined rate by applying a positive force thereto when said movable means is detected to be moving at a rate less than said predetermined rate; and administering a disciplinary conditioning signal to the person moving said movable means in response to the decrease of the rate of speed of said movable means from said predetermined rate.

* * * * *